United States Patent
Miamidian et al.

(10) Patent No.: US 11,119,094 B2
(45) Date of Patent: Sep. 14, 2021

(54) AQUEOUS CITRATE-BUFFERED METAL SOLUTIONS

(71) Applicant: CD DIAGNOSTICS, INC., Claymont, DE (US)

(72) Inventors: John Leon Miamidian, Philadelphia, PA (US); Martin Raymond Gould, Mullica Hill, NJ (US); Michael Brown, North East, MD (US)

(73) Assignee: CD DIAGNOSTICS, INC., Claymont, DE (US)

( * ) Notice: Subject to any disclaimer, the term of this patent is extended or adjusted under 35 U.S.C. 154(b) by 282 days.

(21) Appl. No.: 16/139,728

(22) Filed: Sep. 24, 2018

(65) Prior Publication Data

US 2019/0094210 A1 Mar. 28, 2019

Related U.S. Application Data

(60) Provisional application No. 62/563,833, filed on Sep. 27, 2017.

(51) Int. Cl.
*G01N 33/52* (2006.01)
*G01N 33/84* (2006.01)
*G01N 33/50* (2006.01)

(52) U.S. Cl.
CPC ......... *G01N 33/52* (2013.01); *G01N 33/5091* (2013.01); *G01N 33/5094* (2013.01); *G01N 33/84* (2013.01)

(58) Field of Classification Search
CPC .... G01N 33/52; G01N 33/84; G01N 33/5091; G01N 33/5094
See application file for complete search history.

(56) References Cited

U.S. PATENT DOCUMENTS

| | | | | |
|---|---|---|---|---|
| 6,436,259 B1 * | 8/2002 | Russell | ............... | G01N 27/30 204/290.05 |
| 2004/0054160 A1 * | 3/2004 | Pal | ............... | C12Q 1/6806 536/24.3 |
| 2004/0214339 A1 * | 10/2004 | Profitt | ............... | G01N 33/543 436/86 |
| 2005/0136193 A1 * | 6/2005 | Weidman | ............ | H01L 21/76874 427/437 |
| 2007/0020299 A1 * | 1/2007 | Pipkin | ............... | A61K 31/573 424/400 |
| 2009/0162448 A1 * | 6/2009 | Dunwoody | ........... | A61P 17/00 424/490 |
| 2010/0204082 A1 * | 8/2010 | McLaren | ............... | C11D 3/33 510/531 |
| 2011/0315229 A1 * | 12/2011 | Linder | ............... | G01N 33/543 137/1 |
| 2016/0213043 A1 * | 7/2016 | Bulbarello | ............ | A23L 23/10 |

* cited by examiner

*Primary Examiner* — Jennifer Wecker
*Assistant Examiner* — Michael Paul Shimek
(74) *Attorney, Agent, or Firm* — Schwegman Lundberg & Woessner, P.A.

(57) ABSTRACT

Various embodiments disclosed relate to a buffered aqueous solution. The buffered aqueous solution includes a buffer. The buffer includes a citrate component having a concentration in the solution in a range of from about 0.1 mM to about 600 mM. The buffer further includes a metal component having a concentration in the solution in a range of from about 0.01 mM to about 100 mM. The buffered aqueous solution has a pH in a range of from about 5 to about 9.

20 Claims, No Drawings

AQUEOUS CITRATE-BUFFERED METAL SOLUTIONS

CLAIM OF PRIORITY

This application claims the benefit of U.S. Provisional Patent Application Ser. No. 62/563,833, filed on Sep. 27, 2017, the benefit of priority of which is claimed hereby, and which is incorporated by reference herein in its entirety.

BACKGROUND

Stock solutions of metals can be used for various assays to determine whether a metal can be safely used in an implant. In order to effectively test a cellular response, the metals should be in solution at a pH that correlates to a physiological pH. A problem, however, is that metals have a tendency to precipitate out of solution at physiological pH.

SUMMARY OF THE DISCLOSURE

According to various embodiments, a buffered aqueous solution includes a buffer. The buffer includes a citrate component having a concentration in the solution in a range of from about 0.1 mM to about 600 mM. The buffer further includes a metal component having a concentration in the solution in a range of from about 0.01 mM to about 100 mM. The buffered aqueous solution has a pH in a range of from about 5 to about 9.

According to further embodiments, a method of making the buffered aqueous solution is disclosed. The buffered aqueous solution includes a buffer. The buffer includes a citrate component having a concentration in the solution in a range of from about 0.1 mM to about 600 mM. The buffer further includes a metal component having a concentration in the solution in a range of from about 0.01 mM to about 100 mM. The buffered aqueous solution has a pH in a range of from about 5 to about 9. The method includes mixing the metal component, the buffer component, and water to form a mixture. At least one of an acid and a base are added to the mixture to form the aqueous solution.

According to further embodiments, a product for performing an assay includes a buffered aqueous solution including a buffer. The buffer includes a citrate component having a concentration in the solution in a range of from about 0.1 mM to about 600 mM. The buffer further includes a metal component having a concentration in the solution in a range of from about 0.01 mM to about 100 mM. The buffered aqueous solution has a pH in a range of from about 5 to about 9. The product further includes a biological sample.

According to further embodiments, a method of performing an assay includes providing or receiving a biological sample. The biological sample is contacted with a buffered aqueous solution including a buffer. The buffer includes a citrate component having a concentration in the solution in a range of from about 0.1 mM to about 600 mM. The buffer further includes a metal component having a concentration in the solution in a range of from about 0.01 mM to about 100 mM. The buffered aqueous solution has a pH in a range of from about 5 to about 9. Output data is then received.

There are various reasons to use the buffered aqueous solution according to various embodiments of the present invention, including the following non-limiting examples. According to some examples, including a citrate component in the buffered aqueous solution can help to keep the metal component in the solution for a longer period of time than a corresponding buffered aqueous solution that is free of the citrate component. According to some examples, the buffered aqueous solution can retain the metal component in solution at a pH where cells in an assay can retain viability. According to some examples, the citrate component of the buffered aqueous solution can be beneficial in that citrate is a material that is present in cells naturally. Therefore, the presence of citrate in an assay from the buffered aqueous solution may not have an effect on the viability of the cells in the assay.

DETAILED DESCRIPTION

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "allergic reaction" as used herein refers to a hypersensitive reaction of the immune system to a foreign substance.

The term "metal sensitivity" as used herein refers to a form of allergic reaction that can be caused by exposure to metals.

The term "type IV delayed type hypersensitivity" as used herein refers to a cell-mediated immune response that can take two to three days to develop.

The term "proliferation" as used herein refers to a process that results in an increase of the number of cells.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to, vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

Various examples of this disclosure include a buffered aqueous solution that can be beneficial in keeping metals substantially dissolved in solution at a physiological pH and can include a buffer component. It can be desirable to assay metals against biological samples such as cells for many reasons, such as determining whether a patient has an allergy to a particular metal. In order to effectively assay the metals, however, the buffered aqueous solution, amongst other factors, should have a pH at or at least around a physiological pH. The physiological pH refers generally to a pH where the cells remain viable upon exposure to the buffered aqueous solution. However, it can be difficult to bring a buffered aqueous solution including the metals to a physiological pH without the metals precipitating out of the solution. According to this disclosure, a buffered aqueous solution that is effective in substantially retaining the metal in solution includes a citrate component.

The citrate component can be in the buffered aqueous solution at a concentration in a range of from about 0.1 millimolar (mM) to about 600 mM, about 20 mM to about 50 mM, or less than, equal to, or greater than about 0.1 mM, 0.15, 0.2, 0.5, 1, 1.5, 2, 2.5, 3, 5, 10, 20, 30, 40, 50, 60, 70, 80, 90, 100, 110, 120, 130, 140, 150, 160, 170, 180, 190, 200, 310, 320, 330, 340, 350, 360, 370, 380, 390, 400, 410, 420, 430, 440, 450, 460, 470, 480, 490, 500, 510, 520, 530, 540, 550, 560, 570, 580, 590, or about 600 mM. In the buffer component, the citrate component ranges from about 0.01 wt % to about 60 wt % of the buffer component, about 10 wt % to about 30 wt %, or less than, equal to, or greater than about 10 wt %, 15, 20, 25, 30, 35, 40, 45, 50, 55, or 60% of the buffer component.

One or more citrates of the citrate component can include citric acid, a salt of a citric acid, an ester of a citric acid, or a mixture thereof. Citric acid has three carboxyl groups with three pKa values. Derivatives of citric acid can include citrates such as salts or esters of citric acids. The citrates can form anions having a formal charge of −1, −2, or −3. Formula I is a structure showing an example of a citrate with a formal charge of −1:

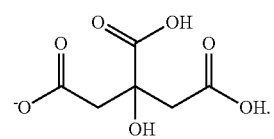

Formula I

Formula II is a structure showing an example of a citrate with a formal charge of −2:

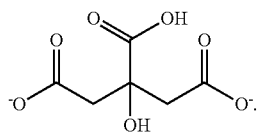

Formula II

Formula III is a structure showing an example of a citrate with a formal charge of −3:

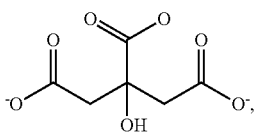

Formula III

Any one of these citrates can form a salt with one or more cations. Examples of cations include sodium and potassium. An example of a citrate salt is trisodium citrate.

The one or more citrates can also be an ester derivative of citric acid. Formula IV is a structure showing an example of an ester derivative of citric acid:

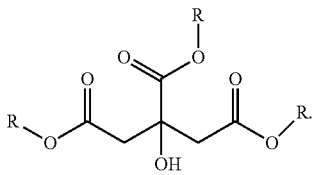

Formula IV

At each occurrence R is independently chosen from substituted or unsubstituted —OH, $(C_1$-$C_{40})$alkyl, $(C_1$-$C_{40})$alkenyl, $(C_1$-$C_{40})$haloalkyl, or $(C_4$-$C_{12})$aryl. An example of ester of citric acid is triethyl citrate. In some examples any one or more of the —R groups can be removed to form an ester salt. Formula V is a structure showing an ester of a citric acid with a formal charge of −1:

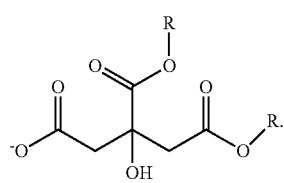

Formula V

Formula VI is a structure showing an ester of a citric acid with a formal charge of −2:

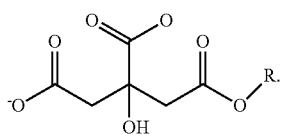

Formula VI

Any of the one or more citrates has the ability to chelate or otherwise bond to a metal. Given the presence of the three carbonyl groups, the chelation between an individual citrate and a metal can be characterized as monodentate (one bond between the citrate and the metal), bidentate (two bonds between the citrate and the metal), or tridentate (three bonds between the citrate and the metal). The role of the citrate can vary. For example, the citrate can act exclusively as a buffer and can be mixed with chelators such as EDTA. The citrate can act entirely as a chelator and additional buffering components can be added to solution to bring the solution to a physiological pH. The citrate can function as both a chelator and a buffering component. One reason to include a secondary buffer is that the concentration of any one particular buffer can be controlled to not be so high to cause damage to a biological system such as a cell culture while still maintaining a physiological pH.

Other buffer components can include a structure according to Formula VII:

Formula VII

At each occurrence R is independently chosen from —H, substituted or unsubstituted —OH, $(C_1$-$C_{40})$alkyl, $(C_1$-$C_{40})$alkenyl, $(C_1$-$C_{40})$alkoxy, $(C_1$-$C_{40})$haloalkyl, or $(C_4$-$C_{12})$aryl.

Other buffer components can include a structure according to Formula VIII:

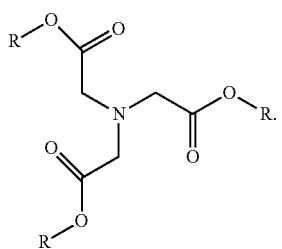

Formula VIII

At each occurrence R is independently chosen from —H, substituted or unsubstituted —OH, $(C_1$-$C_{40})$alkyl, $(C_1$-$C_{40})$alkenyl, $(C_1$-$C_{40})$haloalkyl, or $(C_4$-$C_{12})$aryl.

Other buffer components can include a structure according to Formula IX:

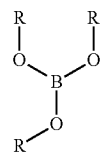

At each occurrence R is independently chosen from —H, substituted or unsubstituted —OH, $(C_1$-$C_{40})$alkyl, $(C_1$-$C_{40})$alkenyl, $(C_1$-$C_{40})$haloalkyl, or $(C_4$-$C_{12})$aryl.

The metal component in the buffered aqueous solution can have a concentration in a range of from about 0.1 mM to about 10 mM, about 3 mM to about 7 mM, or less than, equal to, or greater than about 0.01 mM, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 50, 50.5, 51, 51.5, 52, 52.5, 53, 53.5, 54, 54.5, 55, 55.5, 56, 56.5, 57, 57.5, 58, 58.5, 59, 59.5, 60, 60.5, 61, 61.5, 62, 62.5, 63, 63.5, 64, 64.5, 65, 65.5, 66, 66.5, 67, 67.5, 68, 68.5, 69, 70, 70.5, 71, 71.5, 72, 72.5, 73, 73.5, 74, 74.5, 75, 75.5, 76, 76.5, 77, 77.5, 78, 78.5, 79, 79.5, 80, 80.5, 81, 81.5, 82, 82.5, 83, 83.5, 84, 84.5, 85, 85.5, 86, 86.5, 87, 87.5, 88, 88.5, 89, 89.5, 90, 90.5, 91, 91.5, 92, 92.5, 93, 93.5, 94, 94.5, 95, 95.5, 96, 96.5, 97, 97.5, 98, 98.5, 99, 99.5, or about 100 mM. The metal component can also be in a range of from about 0.000018 wt % to about 5 wt % of the solution, about 0.00004 wt % to about 0.15 wt %, or less than, equal to, or greater than about 0.000018 wt %, 0.00004, 0.0001, 0.005, 0.01, 0.1, 0.5, 1, 3, or 5 wt % of the buffered aqueous solution. Table 1 shows examples of suitable concentrations of metals in the buffered aqueous solution.

metals, about 80 wt % to about 100 wt %, or less than, equal to, or greater than about 50 wt %, 55, 60, 65, 70, 75, 80, 85, 90, 95, or 100 wt %. Correspondingly, the portion of the one or more citrates chelated with the one or more metals can be in a range of from about 50 wt % to about 100 wt % of the one or more citrates, about 80 wt % to about 100 wt %, or less than, equal to, or greater than about 50 wt %, 55, 60, 65, 70, 75, 80, 85, 90, 95, or 100 wt %.

Chelation between the one or more citrates and the one or more metals can help to solubilize at least a portion of the one or more metals in the buffered aqueous solution. The portion of the one or more solubilized metals can be in a range of from about 70 wt % to about 100 wt % of the one or more metals, about 95 wt % to about 100 wt %, or less than, equal to, or greater than about 70 wt %, 75, 80, 85, 90, 95, or 100 wt %. The solubilization of the one or more metals can be such that the buffered aqueous solution is substantially free of a precipitate comprising the metal component. The amount of the one or more metals dissolved in the buffered aqueous solution can remain substantially constant (e.g., within about 0.5% to about 10%) for a period of time exceeding at least two hours. For example, the dissolved amount of the one or more metals can remain substantially constant for a period of time in range of from

TABLE 1

Metal Concentrations in Buffered Aqueous Solutions.

| Metal | Atomic Mass | starting stock mg/ml | 10,000 ug/ml stating stocks (1.0%) mM conc. | 10 mM mg/ml | 10 mM wt % | 0.1 mM wt % |
|---|---|---|---|---|---|---|
| Nickel | 58.7 | 10 | 170.39 | 0.587 | 0.06 | 0.000587 |
| cobalt | 58.9 | 10 | 169.69 | 0.589 | 0.06 | 0.000589 |
| chromium | 52.0 | 10 | 192.32 | 0.52 | 0.05 | 0.00052 |
| Titanium | 47.9 | 10 | 208.91 | 0.479 | 0.05 | 0.000479 |
| Tantalum | 180.9 | 10 | 55.26 | 0.018 | 0.00 | 0.000018 |
| Aluminum | 27.0 | 10 | 370.64 | 0.270 | 0.03 | 0.00027 |
| Zirconium | 91.2 | 10 | 109.63 | 0.912 | 0.09 | 0.000912 |
| Vanadium | 50.9 | 10 | 196.31 | 0.509 | 0.05 | 0.000509 |
| Molybendum | 95.9 | 10 | 104.23 | 0.959 | 0.10 | 0.000959 |

One or more metals of the metal component can be in a range of from about 50 wt % to about 100 wt % of the metal component, about 95 wt % to about 100 wt %, or less than, equal to, or greater than about 50 wt %, 55, 60, 65, 70, 75, 80, 85, 90, 95, or 100 wt %. The one or more metals can be many suitable metals. Examples of suitable metals include hydrated or elemental nickel, chromium, cobalt, vanadium, titanium, tantalum, zirconium, aluminum, molybdenum, complexes thereof, alloys thereof, or salts thereof.

In examples of the one or more metals where the metals are complexes, the metals can coordinate with or have a ligand bonded thereto. Examples of suitable ligands includes -acetylacetonato, -amine, -2,2-bipyridine, -bromo, -carbanato, -carbonyl, -chloro, -cyano, -diethylenetriamine, -bis(diphenylphosphino)ethane, -bis(diphenylphosphino)methane, -cyclopentadienyl, -ethylenediamine, -ethylenendiaminetetraacetato, -fluoro, -glycinato, -hydrido, -hydroxox, -iodo, -isothiocyanato, -nitrato, -nitrito, -nitro, -oxo, -oxalate, -pyridine, -sulfide, -tetraazacyclotetradecane, -thiocyanato, -thiolato, -triaminotriethylamine, -tricyclohexylphosphine, -triethylphosphine, -trimethylphosphine, and -triphenylphosphine.

In the buffered aqueous solution at least a portion of the one or more metals are chelated with at least a portion of the one or more citrates. The portion of the one or more metals chelated with the one or more citrates can be in a range of from about 50 wt % to about 100 wt % of the one or more about 2 hours to about 1 year, about 1 month to about 6 months, or less than equal to, or greater than about 2 hours, 12 hours, 1 day, 1 week, 2 weeks 1 month, 2 months, 3 months, 4 months, 5 months, 6 months, 7 months, 8 months, 9 months, 10 months, 11 months or 1 year.

The pH of the buffered aqueous solution can be tuned to any suitable range. For example, the pH of the buffered aqueous solution can be in a range of from about 5 to about 9, about 6.5 to about 7.8, or less than, equal to, or greater than about 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, or about 9.

In some examples, the buffered aqueous solution can include a second buffer component. The second buffer component can be different than the buffer component, including citrate, described above Examples of suitable second buffer components include any chosen from phosphate, borate, bicarbonate, carbonate, lactate, 2-[4-(2-hydroxyethyl)piperazin-1-yl]ethanesulfonic acid, [tris(hydroxymethyl)methylamino]propanesulfonic acid, 2(bis(2-hydroxyethyl)amino)acetic acid, tris(hydroxymethyl)aminomethane, N-(2-hydroxy-1,1-bis(hydroxymethyl)ethyl)glycine, 3-[[1,3-dihydroxy-2-(hydroxymethyl)propan-2-yl]amino]-2-hydroxypropane-1-sulfonic acid, 2-[[1,3-dihydroxy-2-(hydroxymethyl)propan-2-yl]amino]ethanesulfonic acid, (3-(N-morpholino)propanesulfonic acid), piperazine-N,N'-bis(2-ethanesulfonic acid), dimethylarsinic acid, 2-(N-morpholino)ethanesulfonic acid, nitrilotriacetic acid, or a mixture thereof. The second buffer component can be present in the buffered aqueous solution in a concentration in a range of from about 2 mM to about 600 mM.

The buffered aqueous solution can be made in any suitable manner. For example, a method of making the buffered aqueous solution can include forming a mixture of the buffer component, the metal component, and water. The buffer component can include, for example, sodium citrate or a mixture of citric acid and sodium phosphate. The metal component can be in the form of a powder or can come from a stock solution of the metal component dissolved in a low pH acidic solution. The acid used to dissolve the metal component can be chosen form hydrochloric acid, nitric acid, hydrofluoric acid, or a mixture thereof. The amount of water added can depend on the desired pH of the mixture and the desired volume of the mixture.

To bring the buffered aqueous solution to its final concentration, a quantity of at least one of an acid and a base is added to the mixture. The acid or the base can be added in a drop-wise manner while the mixture is spun or agitated. An example of an acid that can be used to lower the pH of the buffered aqueous solution can include 5% nitric acid. An example of a base that can be used to raise the pH of the buffered aqueous solution can include 10M NaOH.

To remove any solid material, if present, the buffered aqueous solution can be filtered through a filter. In some embodiments the filter can be a surfactant-free filter. The filter can be about a 0.2 micron to about a 2 micron filter, about a 0.5 micron to about a 1 micron filter, or less than, equal to, or greater than about a 0.2 micron, 0.3, 0.4, 0.5, 0.6, 0.7, 0.8, 0.9, 1.0, 1.1, 1.2, 1.3, 1.4, 1.5, 1.6, 1.7, 1.8, 1.9, or about a 2 micron filter.

Once all the components of the buffered aqueous solution are mixed, the solution can be stored in any suitable container. Examples of suitable containers include a container including a polymer or plastic, such as an acid-washed high density polyethylene or a low density polyethylene. The buffered aqueous solution can be stored at a temperature in a range of from about 0° C. to about 50° C., about 10° C. to about 40° C., or less than equal to, or greater than about 0° C., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C.

There are many suitable ways to use the buffered aqueous solution. An example of a suitable use includes incorporating the buffered aqueous solution into a product for performing an assay. Examples of suitable assays include at least one of a lymphocyte transformation test, a flow cytometry test, a macrophage migration inhibition assay, and a leukocyte migration-inhibition test.

The product can include a biological sample. The biological sample can include one or more cells, which can be prokaryotic or eukaryotic cells. In certain examples, the eukaryotic cells can be lymphocytes. To maintain viability of the cells the product can include a cell culture medium that includes nutrients or other components useful for promoting cell growth and health. An example of a suitable medium can include an RPMI 1640 with 25 mM Hepes medium available from Sigma-Aldrich.

The buffered aqueous solution can be diluted by the cell culture medium. The buffered aqueous solution can, for example, have a 10 mM concentration of metals in the citrate buffer. This can be further dissolved 10× in RPMI media including 25 mM HEPES this is then diluted 10-fold in a cell culture media in plate well. This brings the total dilution of the metal to 100-fold.

EXAMPLES

Various embodiments of the present disclosure can be better understood by reference to the following Examples which are offered by way of illustration. The present disclosure is not limited to the Examples given herein.

Example 1

Preparation of a Citric Acid-Sodium Phosphate Buffer in a pH Range of 2.6-7.6

A 0.1 M solution of citric acid monohydrate, $C_6H_8O_7H_2O$ (21.01 g/l) and a 0.2 M solution of $Na_2HPO_4 \cdot 12H_2O$ (71.64 g/L) were prepared. To achieve a desired pH the volumes shown in the Table 2 were mixed. Alternatively the masses shown in Table 1 can be dissolved in water and mixed with the final volume of the solution being brought to 100 cm$^3$ with water

TABLE 2

| | Citric Acid-Sodium Phosphate Buffer | | | |
|---|---|---|---|---|
| | Citric acid | | $Na_2HPO_4 \cdot 12H_2O$ | |
| pH at 25° C. | Volume of 0.1M solution (cm$^3$) | Mass in 100 cm$^3$ (g) | Volume of 0.2M solution (cm$^3$) | Mass in 100 cm$^3$ (g) |
| 2.6 | 89.1 | 1.87 | 10.9 | 0.78 |
| 2.8 | 84.15 | 1.77 | 15.85 | 1.14 |
| 3.0 | 79.45 | 1.67 | 20.55 | 1.47 |
| 3.2 | 75.3 | 1.58 | 24.7 | 1.77 |
| 3.4 | 71.5 | 1.50 | 28.5 | 2.04 |
| 3.6 | 67.8 | 1.42 | 32.2 | 2.31 |
| 3.8 | 64.5 | 1.36 | 35.5 | 2.54 |
| 4.0 | 61.45 | 1.29 | 38.55 | 2.76 |
| 4.2 | 58.6 | 1.23 | 41.4 | 2.97 |
| 4.4 | 55.9 | 1.17 | 44.1 | 3.16 |
| 4.6 | 53.25 | 1.12 | 46.75 | 3.35 |
| 4.8 | 50.7 | 1.07 | 49.3 | 3.53 |
| 5.0 | 48.5 | 1.02 | 51.5 | 3.69 |
| 5.2 | 46.4 | 0.97 | 53.6 | 3.84 |
| 5.4 | 44.25 | 0.93 | 55.75 | 3.99 |
| 5.6 | 42.0 | 0.88 | 58.0 | 4.16 |
| 5.8 | 39.55 | 0.83 | 60.45 | 4.33 |
| 6.0 | 36.85 | 0.77 | 63.15 | 4.52 |
| 6.2 | 33.9 | 0.71 | 66.1 | 4.74 |
| 6.4 | 30.75 | 0.65 | 69.25 | 4.96 |
| 6.6 | 27.25 | 0.57 | 72.75 | 5.21 |
| 6.8 | 22.75 | 0.48 | 77.25 | 5.53 |
| 7.0 | 17.65 | 0.37 | 82.35 | 5.90 |
| 7.2 | 13.05 | 0.27 | 86.95 | 6.23 |
| 7.4 | 9.15 | 0.19 | 90.85 | 6.51 |
| 7.6 | 6.35 | 0.13 | 93.65 | 6.71 |

Example 2

Stability of Metal Stock Solutions Including Citrate-Buffered Aqueous Solutions

Stability (shelf-life) for standardized metals used in a metal sensitivity lymphocyte transformation test were studied.

Metal solutions were developed. The concentration of each metal in solution was measured initially at set time points as shown in Tables 3 and 4. The pH of the solutions are shown in Table 5. The metal solutions were stabilized with 50 mM citrate buffer.

Metal solutions including citrate were diluted 10-fold in tissue culture media (RPMI 1640 with 25 mM HEPES) and were monitored weekly for 5 weeks. These represent the 10× concentrate the tissue culture personnel would make and sterile filter for delivery into samples of cells at a final 1× dose. Both filtered (0.2. μm sterile filtration) and unfiltered material were tested out to a 5-week time period. Results are summarized in the Table 7.

TABLE 3

Real Time Stability at Ambient Temperature
(100X filtered concentrates)

| Metals units | label value mM | 5 weeks mM | 9 weeks mM | 19 weeks mM |
|---|---|---|---|---|
| Ti | 10.00 | 9.97 | 9.82 | 10.07 |
| V | 1.00 | 1.02 | 1.01 | 1.03 |
| Co | 1.00 | 1.02 | 1.00 | 1.01 |
| Ta | 10.00 | 9.51 | 9.55 | 9.98 |
| Cr | 10.00 | 9.95 | 9.49 | 9.84 |
| Ni | 10.00 | 9.63 | 9.75 | 10.36 |
| Zr | 10.00 | 10.62 | 9.69 | 10.47 |

TABLE 4

Real Time Stability at Ambient Temperature
(100X filtered concentrates)

| metals units | label value mM | 5 weeks % | 9 weeks % | 19 weeks % |
|---|---|---|---|---|
| Ti | 10.00 | 99.70 | 98.17 | 100.66 |
| V | 1.00 | 101.61 | 100.91 | 103.04 |
| Co | 1.00 | 101.87 | 100.32 | 100.97 |
| Ta | 10.00 | 95.12 | 95.52 | 99.81 |
| Cr | 10.00 | 99.53 | 94.95 | 98.35 |
| Ni | 10.00 | 96.29 | 97.55 | 103.57 |
| Zr | 10.00 | 106.16 | 96.90 | 104.65 |

TABLE 5 pH of Stock Solutions Stored at Ambient Temperature (100X filtered concentrates)

| Metals | Starting pH | pH Jun. 9, 2017 (116 days) | Difference |
|---|---|---|---|
| Ti | 7.2 | 7.24 | 0.04 |
| V | 7.2 | 7.36 | 0.16 |
| Co | 7.2 | 8.00 | 0.80 |
| Ta | 7.2 | 6.90 | −0.30 |
| Cr | 7.2 | 7.58 | 0.38 |
| Ni | 7.2 | 7.85 | 0.65 |
| Zr | 7.2 | 6.88 | −0.32 |
| Nitric acid vehicle | 7.25 | 7.52 | 0.27 |
| Fluoride vehicle | 7.27 | 7.36 | 0.09 |

TABLE 6

Accelerated Stability of (100X Filtered Concentrates)
Stock Metal solutions in Final Packaging

| metals | Label values mM | Days at 75° C. | | | | |
|---|---|---|---|---|---|---|
| | | 0 % Recovery | 5 % Recovery | 10 % Recovery | 15 % Recovery | 20 % Recovery |
| Ti | 10 | 100.66 | 100.42 | 102.02 | 97.77 | 95.15 |
| V | 1 | 103.04 | 101.33 | 104.18 | 103.02 | 101.92 |
| Co | 1 | 100.97 | 101.10 | 102.32 | 105.89 | 102.58 |
| Ta | 10 | 99.81 | 98.09 | 100.70 | 95.46 | 100.89 |
| Cr | 10 | 98.38 | 99.97 | 102.31 | 97.70 | 103.13 |
| Ni | 10 | 103.57 | 101.27 | 100.12 | 101.63 | 104.44 |
| Zr | 10 | 104.65 | 103.35 | 105.16 | 104.69 | 107.24 |

Accelerated calculations were based using the 10-degree (Q10) rule described in Clin. Chem 37;3, pp 398-402. Q10 was assumed to be 2, with Ea (Kcal/mol)=12.2 and Q10=1.8 Ea(Kcal/mol)=11 for a 10% safety factor. The results are shown in Table 5. Projected stability was at ambient, assumed to be 22° C. Projected stability used the Arrhenius equation: Time at 22° C.=(time at 75° C.)× $Q10^{((75°\ C.-22°\ C.)/10)}$

TABLE 7

Stability of metals diluted in RPMI HEPES (10X Concentrates)

| | Label value | Unfiltered All values in mM | | | | | filtered All values in mM | | | | |
|---|---|---|---|---|---|---|---|---|---|---|---|
| Metals | | Week1 | Week2 | Week3 | Week4 | Week 5 | Week 1 | Week2 | Week3 | Week 4 | Week 5 |
| Ti | 1.00 | 1.02 | 0.98 | 0.99 | 1.02 | 0.99 | 1.01 | 0.99 | 0.98 | 0.97 | 0.98 |
| Zr | 1.00 | 1.01 | 1.01 | 0.99 | 0.93 | 0.92 | 1.08 | 1.04 | 0.96 | 1.00 | 0.95 |
| Ni | 1.00 | 0.97 | 0.97 | 0.99 | 0.97 | 0.97 | 0.93 | 0.97 | 1.01 | 0.98 | 0.98 |
| Cr | 1.00 | 0.99 | 0.98 | 0.98 | 0.99 | 0.97 | 0.96 | 0.99 | 0.97 | 1.00 | 0.97 |
| Co | 0.10 | 0.10 | 0.10 | 0.10 | 0.10 | 0.10 | 0.10 | 0.10 | 0.10 | 0.11 | 0.10 |
| Ta | 1.00 | 0.97 | 0.92 | 0.90 | 0.90 | 0.90 | 0.94 | 0.95 | 0.95 | 0.96 | 0.90 |
| V | 0.10 | 0.10 | 0.10 | 0.10 | 0.10 | 0.10 | 0.10 | 0.10 | 0.10 | 0.10 | 0.10 |
| | Label value | All values in % Recovery | | | | | All values in % Recovery | | | | |
| Metals | | Week 1 | Week2 | Week3 | Week4 | Week 5 | Week 1 | Week2 | Week3 | Week 4 | Week 5 |
| Ti | 1.00 | 102.21 | 97.99 | 98.79 | 101.49 | 98.79 | 100.74 | 98.68 | 97.48 | 97.05 | 97,88 |
| Zr | 1.00 | 100.49 | 100.60 | 99.35 | 92.84 | 92.29 | 107.74 | 103.50 | 96.06 | 99.38 | 95.36 |
| Ni | 1.00 | 97.21 | 97.87 | 99.04 | 97.89 | 97.36 | 93.63 | 97.73 | 101.76 | 98.59 | 98.66 |
| Cr | 1.00 | 98.58 | 97.84 | 97.81 | 99.30 | 96.64 | 96.50 | 98.56 | 97.46 | 100.31 | 97.45 |
| Co | 0.10 | 101.37 | 100.38 | 98.13 | 100.36 | 100.03 | 103.03 | 101.13 | 103.40 | 105.52 | 101.26 |

TABLE 7-continued

Stability of metals diluted in RPMI HEPES (10X Concentrates)

| Ta | 1.00 | 97.08 | 92.33 | 89.70 | 89.82 | 90.29 | 93.60 | 94.77 | 94.85 | 95.68 | 90.07 |
| V | 0.10 | 103.27 | 98.15 | 103.65 | 100.39 | 102.60 | 104.00 | 101.88 | 101.69 | 103.67 | 99.87 |

All of the stock solutions of metals in citrate (mM for Co, V; 10 mM for Ti, Ta, Cr, Ni, Zr) showed real time stability of at least 4 months for the initial pilots prepared at SPEX Certiprep. In accelerated testing, the solutions of metals in citrate are projected to have shelf life of at least 1.23 years. On 10-fold dilution into RPMI 1640 with 25 mM Hepes all of these metals showed greater than 5 weeks real time stability at ambient temperature filtered (0.2 μm sterile filtration) or unfiltered. These solutions are the 10× metal stocks used to dilute into the wells with cells.

Example 3

Lymphocyte Transformation Test (LTT)

The Lymphocyte Transformation Test used for Metal Sensitivity Testing measures cell proliferation relative to a negative control. In the results shown in Table 8, an SI (stimulation index)≥4 is considered positive. For the polkweed mitogen (PWM) or any other suitable mitogen positive control, an SI≥30 is required for the assay to be considered a valid run.

TABLE 8

Stimulation Index Data

| Subject | | Stimulant | | | | | |
|---|---|---|---|---|---|---|---|
| ID | Date | PWM | Cr | Co | Ni | Ti | V |
| 71390 | 4 Nov. 2016 | 119.6 | 0.86 | 1 | 37.82 | nd | nd |
| | 11 Jan. 2017 | 128.6 | 0.14 | 0.24 | 9.25 | 5.03 | 8.73 |
| 20112 | 11 Nov. 2016 | 669.51 | 2.87 | 1.68 | 104.83 | 2.15 | 0.57 |
| | 11 Jan. 2017 | 691.43 | 0.93 | 0.61 | 18.82 | 2.53 | 5.56 |
| 19A | 15 Jul. 2016 | 124 | 3.2 | 0.9 | 22.6 | nd | nd |
| | 6 Dec. 2016 | 108.15 | 1.33 | 0.91 | 15.59 | nd | nd |
| 21R | 19 Jul. 2016 | 223 | 1 | 0 | 5 | nd | 1 |
| | 3 Feb. 2017 | 75.85 | 14.75 | 15.91 | 52.35 | 1.15 | 2 |

The data in Table 8 demonstrates the function of a cell based assay (e.g., a lymphocyte transformation test) with subjects that respond to nickel. As shown in Table 8, prior to December 2016, the assay was run without citrate, and as of December 2016 the assay incorporated citrate as the metal stabilizer. Nickel dissolution at physiological pH was not a notable problem as was stabilization of other metals including titanium, tantalum, chromium, and zirconium. Therefore, much like the positive control, this data shows the assay functioning equally well before and after the incorporation of citrate amongst four separate subjects.

Example 4

Lymphocyte Transformation Test in the Presence of Metals

The data described herein demonstrates the function of a cell based assay (e.g., a lymphocyte transformation test) in the presence of metals available for testing and whether those metals are toxic. In this example, each metal tested was stabilized with citrate. In addition, the assay was performed in the presence of positive control and none of the metals tested mitigated assay function in this context.

Results of the first phase of analysis using four donors is summarized in the following tables below. As expected, and as is commonly observed stimulation indices for different donors varies as shown in Table 9. For each donor, results were normalized and expressed as a percent of the positive control stimulation, shown in Table 10.

TABLE 9

Stimulation Index for PWM in the presence of 0.1 mM metals

| Metal | Donor LS 23 89053D | Donor LS 23 89054C | Donor LS 23 89058C | Donor LS 23 89063E |
|---|---|---|---|---|
| Aluminum | 201 | 52 | 246 | 341 |
| Chromium | 195 | 45 | 221 | 376 |
| Cobalt | 39 | 5 | 16 | 7 |
| Molybdenum | 181 | 54 | 211 | 374 |
| Nickel | 184 | 43 | 198 | 222 |
| Tantalum | 185 | 64 | 252 | 243 |
| Titanium | 143 | 41 | 165 | 272 |
| Vanadium | 2 | 1 | 0 | 3 |
| Zyrconium | 209 | 49 | 246 | 369 |
| Vehicle | 217 | 51 | 261 | 349 |
| PWM Control | 217 | 40 | 202 | 362 |

TABLE 10

Percent of Positive Control in the Presence of 0.1 mM Metals

| Metal | Donor LS 23 89053D | Donor LS 23 89054C | Donor LS 23 89058C | Donor LS 23 89063E | AVERAGE |
|---|---|---|---|---|---|
| Aluminum | 92.50 | 130.40 | 121.66 | 94.35 | 109.73 |
| Chromium | 89.93 | 111.93 | 109.19 | 103.94 | 103.75 |
| Cobalt | 18.13 | 12.40 | 8.03 | 1.82 | 10.09 |
| Molybdenum | 83.37 | 135.55 | 104.56 | 103.33 | 106.70 |
| Nickel | 84.91 | 106.73 | 98.01 | 61.52 | 87.79 |
| Tantalum | 85.38 | 160.63 | 124.50 | 67.17 | 109.42 |
| Titanium | 66.02 | 102.08 | 81.57 | 75.25 | 81.23 |
| Vanadium | 0.73 | 1.35 | 0.22 | 0.70 | 0.75 |
| Zyrconium | 96.40 | 122.68 | 121.59 | 101.94 | 110.65 |
| Vehicle | 99.99 | 126.70 | 129.30 | 96.55 | 113.13 |

Based on the above results, both cobalt and vanadium exhibited significant toxicity at 0.1 mM. A second phase was then undertaken with two normal donors where these metals were titrated down to determine the level with minimal toxicity. Table 11 shows the stimulation index with titration. For each donor results were normalized and expressed as a percent of the positive control stimulation, shown in the Table 12.

TABLE 11

Stimulation Index in Cobalt and Vanadium Titrations

| Cobalt mM | Donor LS 55 54645C | Donor LS 55 54647C | Vanadium mM | Donor LS 55 54645C | Donor LS 55 54647C |
|---|---|---|---|---|---|
| 0 | 380.82 | 636.89 | 0 | 380.82 | 636.89 |
| 0.1 | 10.22 | 14.10 | 0.1 | 1.02 | −0.04 |
| 0.02 | 269.48 | 364.52 | 0.02 | 403.34 | 522.21 |
| 0.01 | 445.68 | 586.09 | 0.01 | 580.65 | 495.53 |
| 0.005 | 342.34 | 569.19 | 0.005 | 399.93 | 704.39 |
| 0.001 | 304.95 | 783.18 | 0.001 | 457.68 | 727.02 |

TABLE 12

Percent of Control in Cobalt and Vanadium Titrations

| Cobalt mM | Donor LS 55 54645C | Donor LS 55 54647C | Vanadium mM | Donor LS 55 54645C | Donor LS 55 54647C |
|---|---|---|---|---|---|
| 0.1 | 2.7 | 2.2 | 0.1 | 0.3 | 0.0 |
| 0.02 | 70.8 | 57.2 | 0.02 | 105.9 | 82.0 |
| 0.01 | 117.0 | 92.0 | 0.01 | 152.5 | 77.8 |
| 0.005 | 89.9 | 89.4 | 0.005 | 105.0 | 110.6 |
| 0.001 | 80.1 | 123.0 | 0.001 | 120.2 | 114.2 |

Final concentrations of metals to be used in the Lymphocyte Transformation Test are recommended as shown in Table 13. These levels should show minimum toxic effect on the mononuclear cells used in the assay. For initial product launch only chromium, cobalt, nickel, titanium, and vanadium will be used.

TABLE 13

Metal Concentrations in Lymphocyte Transformation Test

| Metal | mM |
|---|---|
| Aluminum | 0.1 |
| Chromium | 0.1 |
| Cobalt | 0.01 |
| Molybdenum | 0.1 |
| Nickel | 0.1 |
| Tantalum | 0.1 |
| Titanium | 0.1 |
| Vanadium | 0.01 |
| Zirconium | 0.1 |

Example 5

Visual Observations of Metal Stocks in Buffer Systems

Various 10 mM metal stocks were mixed with various buffer systems. The resulting solutions were observed at various pH values when the solution was at 100×. The visual confirmation of any metal precipitate (ppt) was recorded as shown in the tables below.

TABLE 14

5% Sodium Bicarbonate Buffer and 10 mM Metal Stock Solutions

| Metals | Atomic Mass | Metal Chloride | Observation |
|---|---|---|---|
| Nickel | 58.7 | solution (green) | solution (clear) |
| cobalt | 58.9 | solution (red) | solution (light pink) |
| chromium | 52.0 | PPT (pink) | PPT (gray) |
| Titanium | 47.9 | NA | PPT |
| Tantalum | 180.9 | NA | NA |
| Aluminum | 27.0 | solution (clear) | separated suspension |
| Zirconium | 91.2 | solution (clear) | separated suspension |
| Vanadium | 50.9 | solution (blue green) | solution (clear) |
| Molybdenum | 95.9 | PPT dark wine color coated tube | solution clear |

TABLE 15

5% Sodium Borate Buffer and 10 mM Metal Stock Solutions

| Metals | Atomic Mass | Visual Observation | pH 100X |
|---|---|---|---|
| Nickel | 58.7 | solution clear | 7.4 |
| cobalt | 58.9 | solution light pink | 7.4 |
| chromium | 52.0 | Solution light gray | 7.2 |
| Titanium | 47.9 | PPT (white) | NA |
| Tantalum | 180.9 | PPT (white) | NA |
| Aluminum | 27.0 | solution clear | 7.4 |
| Zirconium | 91.2 | PPT white | 5.5 |
| Vanadium | 50.9 | Solution yellow | 7.2 |
| Molybdenum | 95.9 | solution clear | 7.4 |

TABLE 16

5% HEPES Buffer and 10 mM Metal Stock Solutions

| Metals | Atomic Mass | Visual Observation | pH 100X |
|---|---|---|---|
| Nickel | 58.7 | solution clear | 7.4 |
| cobalt | 58.9 | solution light pink | 7.4 |
| chromium | 52.0 | PPT (gray) | 7.4 |
| Titanium | 47.9 | PPT (white) | NA |
| Tantalum | 180.9 | solution clear | 5.0 |
| Aluminum | 27.0 | solution clear | 7.4 |
| Zirconium | 91.2 | PPT (white) | 3.5 |
| Vanadium | 50.9 | solution yellow | 3.5 |
| Molybdenum | 95.9 | solution clear | 7.4 |

TABLE 17

12 mM Sodium Citrate Buffer and 10 mM Metal Stock Solutions

| Metals | Atomic Mass | Visual Observation | pH 100X |
|---|---|---|---|
| Nickel | 58.7 | solution clear | 2 |
| cobalt | 58.9 | solution light pink | 2 |
| chromium | 52.0 | Solution gray | 2 |
| Titanium | 47.9 | Solution clear | 2 |
| Tantalum | 180.9 | solution clear | 2 |
| Aluminum | 27.0 | solution clear | 2 |
| Zirconium | 91.2 | solution clear | 2 |
| Vanadium | 50.9 | solution light blue | 2 |
| Molybdenum | 95.9 | solution clear | 9.0 |

TABLE 18

500 mM Sodium Citrate Buffer and 10 mM Metal Stock Solutions

| Metals | Atomic Mass | Visual Observation | pH 100X |
|---|---|---|---|
| Nickel | 58.7 | solution light green | 7.4 |
| cobalt | 58.9 | solution light pink | 7.4 |
| chromium | 52.0 | Solution light purple | 7.4 |
| Titanium | 47.9 | Solution clear | 7.4 |
| Tantalum | 180.9 | solution clear | 7.4 |
| Aluminum | 27.0 | solution clear | 7.4 |
| Zirconium | 91.2 | solution clear | 7.4 |
| Vanadium | 50.9 | solution purple | 7.4 |
| Molybdenum | 95.9 | solution clear | 9.5 |

TABLE 19

50 mM Sodium Citrate Buffer and 10 mM Metal Stock Solutions

| Metals | Atomic Mass | Visual Observation | pH 100X | pH Diluted in RPMI and 25 mM HEPES 10X |
|---|---|---|---|---|
| Nickel | 58.7 | solution light green | 4.7 | 6.96 |
| cobalt | 58.9 | solution light pink | 4.7 | 6.93 |
| chromium | 52.0 | Solution light purple | 4.7 | 6.82 |
| Titanium | 47.9 | Solution clear | 5.95 | 7.10 |
| Tantalum | 180.9 | solution clear | 4.5 | 6.38 |
| Aluminum | 27.0 | solution clear | 5.6 | 6.95 |
| Zirconium | 91.2 | solution clear | 2.7 | 6.52 |
| Vanadium | 50.9 | solution purple | 3.13 | 6.53 |
| Molybdenum | 95.9 | solution clear | 9.85 | 7.3 |

Additional Embodiments

The following exemplary embodiments are provided, the numbering of which is not to be construed as designating levels of importance:

Embodiment 1 provides a buffered aqueous solution comprising:
  a buffer comprising:
    a citrate component having a concentration in the solution in a range of from about 0.1 mM to about 600 mM; and
    a metal component having a concentration in the solution in a range of from about 0.01 mM to about 100 mM;
  wherein the buffered aqueous solution has a pH in a range of from about 5 to about 9.

Embodiment 2 provides the buffered aqueous solution of Embodiment 1, wherein the citrate component ranges from about 0.01 wt % to about 60 wt % of the buffer.

Embodiment 3 provides the buffered aqueous solution of any one of Embodiments 1 or 2, wherein the citrate component ranges from about 0.01 wt % to about 20 wt % of the buffer.

Embodiment 4 provides the buffered aqueous solution of any one of Embodiments 1-3, wherein the citrate component comprises one or more citrates.

Embodiment 5 provides the buffered aqueous solution of Embodiment 4, wherein the citrate component is chosen from citric acid, a salt of a citric acid, an ester of a citric acid, or a mixture thereof.

Embodiment 6 provides the buffered aqueous solution of Embodiment 5, wherein the salt of the citric acid is trisodium citrate.

Embodiment 7 provides the buffered aqueous solution of Embodiment 5, wherein the ester of citric acid has the structure:

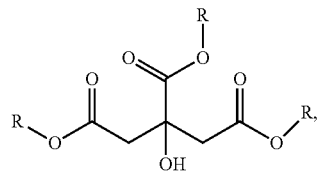

wherein at each occurrence R is independently chosen from substituted or unsubstituted —OH, $(C_1$-$C_{40})$alkyl, $(C_1$-$C_{40})$alkenyl, $(C_1$-$C_{40})$haloalkyl, and $(C_4$-$C_{12})$aryl.

Embodiment 8 provides the buffered aqueous solution of any one of Embodiments 5 or 7 wherein the ester of citric acid is triethyl citrate.

Embodiment 9 provides the buffered aqueous solution of any one of Embodiments 1-8, wherein the citrate component has a concentration in the solution in a range of from about 100 mM to about 500 mM.

Embodiment 10 provides the buffered aqueous solution of any one of Embodiments 1-9, wherein the citrate component has a concentration in the solution in a range of from about 20 mM to about 50 mM.

Embodiment 11 provides the buffered aqueous solution of any one of Embodiments 1-10, wherein the metal component ranges from about 0.000018 wt % to about 5 wt % of the solution.

Embodiment 12 provides the buffered aqueous solution of any one of Embodiments 1-11, wherein the metal component ranges from about 0.0004 wt % to about 0.1 wt % of the aqueous solution.

Embodiment 13 provides the buffered aqueous solution of any one of Embodiments 1-12, wherein the metal component comprises one or more metals.

Embodiment 14 provides the buffered aqueous solution of Embodiment 13, wherein the one or more metals is in a range of from about 50 wt % to about 100 wt % of the metal component.

Embodiment 15 provides the buffered aqueous solution of any one of Embodiments 13 or 14, wherein the one or more metals are chosen from nickel, chromium, cobalt, vanadium, titanium, tantalum, zirconium, aluminum, molybdenum, organometallic complexes thereof, alloys thereof, or salts thereof.

Embodiment 16 provides the buffered aqueous solution of any one of Embodiments 13-15, wherein the metal component is a stock metal solution comprising the metal and an acid.

Embodiment 17 provides the buffered aqueous solution of Embodiment 16, wherein the acid is chosen from hydrochloric acid, nitric acid, fluoride containing acid, and a mixture thereof.

Embodiment 18 provides the buffered aqueous solution of any one of Embodiments 1-17, wherein a concentration of the metal component in the solution is in a range of from about 1 mM to about 10 mM.

Embodiment 19 provides the buffered aqueous solution of any one of Embodiments 13-18, wherein at least a portion of the one or more metals are chelated with at least a portion of the one or more citrates.

Embodiment 20 provides the buffered aqueous solution of Embodiment 19, wherein the portion of the one or more metals is in a range of from about 0.000018 wt % to about 0.1 wt % of the aqueous solution and the portion of the one or more citrates is in a range of from about 0.01 wt % to about 60 wt % of the aqueous solution.

Embodiment 21 provides the buffered aqueous solution of any one of Embodiments 13-20, wherein at least a portion of the one or more metals is dissolved in the aqueous solution.

Embodiment 22 provides the buffered aqueous solution of Embodiment 21, wherein the portion of the one or more dissolved metals is in a range of from about 70 wt % to about 100 wt % of the one or more metals.

Embodiment 23 provides the buffered aqueous solution of any one of Embodiments 21 or 22, wherein the portion of the one or more dissolved metals is in a range of from about 95 wt % to about 100 wt % of the one or more metals.

Embodiment 24 provides the buffered aqueous solution of any one of Embodiments 1-23, wherein the aqueous solution is substantially free of a precipitate comprising the metal component.

Embodiment 25 provides the buffered aqueous solution of any one of Embodiments 21-24, wherein the amount of the one or more metals dissolved in the solution remains constant for a period of time in a range of from about 2 hours to about 1 year.

Embodiment 26 provides the buffered aqueous solution of any one of Embodiments 21-25, wherein the amount of the one or more metals dissolved in the solution remains substantially constant for a period of time in a range of from about 1 month to about 6 months.

Embodiment 27 provides the buffered aqueous solution of any one of Embodiments 1-26, wherein the pH of the buffered aqueous solution is in a range of from about 6.5 to about 7.8.

Embodiment 28 provides the buffered aqueous solution of any one of Embodiments 1-27, further comprising a second buffer that is different from the buffer comprising the citrate component and the metal component.

Embodiment 29 provides the aqueous solution of Embodiment 28, wherein the second buffer is chosen from phosphate, borate, bicarbonate, carbonate, lactate, 2-[4-(2-hydroxyethyl)piperazin-1-yl]ethanesulfonic acid, and a mixture thereof.

Embodiment 30 provides the buffered aqueous solution of any one of Embodiments 28 or 29, wherein the second buffer has a concentration in a range of from about 2 mM to about 600 mM.

Embodiment 31 provides the buffered aqueous solution of Embodiment 1, wherein the citrate component is trisodium citrate;
the metal component is chosen from nickel, chromium, cobalt, vanadium, titanium, tantalum, zirconium, aluminum, molybdenum, organometallic complexes thereof, alloys thereof, or salts thereof; and the pH of the buffered aqueous solution is in a range of from about 6.5 to about 7.8.

Embodiment 32 provides a method of making the buffered aqueous solution of any one of Embodiments 1-31, the method comprising:
mixing the metal component, the buffer component, and water to form a mixture; and
adding at least one of an acid and a base to the mixture to form the aqueous solution.

Embodiment 33 provides the method Embodiment 32, further comprising filtering the aqueous solution.

Embodiment 34 provides the method of any one of Embodiments 32 or 33, wherein the acid or the base is added to the mixture in a drop-wise manner.

Embodiment 35 provides the method of any one of Embodiments 32-34, wherein the base is NaOH.

Embodiment 36 provides the method of any one of Embodiments 32-35, wherein the acid is nitric acid.

Embodiment 37 provides the method of any one of Embodiments 32-36, wherein the buffered aqueous solution is in a container comprising at least one of a high density polyethylene and a low density polyethylene.

Embodiment 38 provides the method of any one of Embodiments 32-37, wherein the metal component that is added to the buffer component and the water is a stock solution of the one or more metals dissolved in acid.

Embodiment 39 provides the method of any one of Embodiments 32-38, wherein the metal component that is added to buffer component and the water is a powder.

Embodiment 40 provides a product for performing an assay, the product comprising:
the buffered aqueous solution of any one of Embodiments 1-31 or formed according the method of any one of Embodiments 32-39; and
a biological sample.

Embodiment 41 provides the product of Embodiment 40, wherein the biological sample comprises one or more cells.

Embodiment 42 provides the product of Embodiment 41, wherein the one or more cells are chosen from eukaryotic cells, prokaryotic cells, and a mixture thereof.

Embodiment 43 provides the product of Embodiment 41, wherein the one or more cells are lymphocytes.

Embodiment 44 provides the product of any one of Embodiments 40-43, wherein the product further comprises a cell culture medium.

Embodiment 45 provides the product of Embodiment 44, wherein the buffered aqueous solution is diluted in a range of from about 10× to about 100× in the cell culture medium.

Embodiment 46 provides the product of Embodiment 44, wherein the buffered aqueous solution is diluted in a range of from about 20× to about 80× in the cell culture medium.

Embodiment 47 provides a method of using the product of any one of Embodiments 40-46, the method comprising performing an assay.

Embodiment 48 provides the method of Embodiment 47, wherein the assay is at least one of a lymphocyte transformation test, a flow cytometry test, a macrophage migration inhibition assay, and a leukocyte migration-inhibition test.

Embodiment 49 provides a method of performing an assay, the method comprising:
providing or receiving a biological sample:
contacting the biological sample with the buffered aqueous solution according to any one of Embodiments 1-64 or formed according to the method of any one of Embodiments 32-39; and
receiving output data.

Embodiment 50 provides the method of Embodiment 49, wherein the assay is a lymphocyte transformation test.

Embodiment 51 provides the method of Embodiment 49, wherein the biological sample comprises one or more cells.

Embodiment 52 provides the method of Embodiment 51, wherein the one or more cells are chosen from eukaryotic cells, prokaryotic cells, and a mixture thereof.

Embodiment 53 provides the method of Embodiment 51, wherein the one or more cells are lymphocytes.

Embodiment 54 provides the method of any one of Embodiments 49-53, further comprising providing or receiving a cell culture medium.

Embodiment 55 provides the method of Embodiment 54, further comprising diluting the buffered aqueous solution to a value in a range of from about 10× to about 100× in the cell culture medium.

Embodiment 56 provides the method of Embodiment 54, further comprising diluting the buffered aqueous solution to a value in a range of from about 20× to about 80× in the cell culture medium.

What is claimed is:

1. A buffered aqueous solution comprising:
   water; and
   a buffer comprising
      a citrate component having a concentration in the solution in a range of from about 5 mM to about 50 mM,
      a phosphate component having a concentration in the solution in a range of from about 2 mM to about 600 mM, and
      a metal component having a concentration in the solution in a range of from about 0.01 mM to about 100 mM, wherein a total amount of the metal component in the solution does not increase or decrease more than 10% for a period of time in a range of from about 2 hours to about 1 year, the metal component comprising one or more metals chosen from nickel, chromium, vanadium, titanium, tantalum, zirconium, aluminum, molybdenum, organometallic complexes thereof, alloys thereof, or salts thereof;
   wherein the buffered aqueous solution has a pH in a range of from about 5 to about 9.

2. The buffered aqueous solution of claim 1, wherein the citrate component ranges from about 0.01 wt % to about 60 wt % of the buffer.

3. The buffered aqueous solution of claim 1, wherein the citrate component is chosen from citric acid, a salt of a citric acid, an ester of a citric acid, or a mixture thereof.

4. The buffered aqueous solution of claim 3, wherein the salt of the citric acid is trisodium citrate.

5. The buffered aqueous solution of claim 1, wherein the citrate component has a concentration in the solution in a range of from about 20 mM to about 50 mM.

6. The buffered aqueous solution of claim 1, wherein the metal component ranges from about 0.000018 wt % to about 0.1 wt % of the solution.

7. The buffered aqueous solution of claim 1, wherein the metal component comprises tantalum, an organometallic complex thereof, an alloy thereof, or a salt thereof.

8. The buffered aqueous solution of claim 1, wherein the aqueous solution is substantially free of a precipitate comprising the metal component.

9. The buffered aqueous solution of claim 1, wherein a total amount of the metal component in the solution does not increase or decrease more than 10% for a period of time in a range of from about six months to about 1 year.

10. The buffered aqueous solution of claim 1, wherein the pH of the buffered aqueous solution is in a range of from about 6.5 to about 7.8.

11. The buffered aqueous solution of claim 1, wherein
   the citrate component is trisodium citrate;
   the metal component is chosen from nickel, chromium, cobalt, vanadium, titanium, tantalum, zirconium, aluminum, molybdenum, organometallic complexes thereof, alloys thereof, or salts thereof; and
   the pH of the buffered aqueous solution is in a range of from about 6.5 to about 7.8.

12. A method of making a buffered aqueous solution, the method comprising:
   mixing a metal component, a citrate component, a phosphate component and water to form a mixture; and
   adding at least one of an acid and a base to the mixture to form the buffered aqueous solution;
   wherein
      the citrate component has a concentration in the solution in a range of from about 5 mM to about 50 mM in the buffered aqueous solution,
      the phosphate component has a concentration in the solution in a range of from about 2 mM to about 600 mM,
      the metal component has a concentration in the solution in a range of from about 0.01 mM to about 100 mM in the buffered aqueous solution wherein a total amount of the metal component in the solution does not increase or decrease more than 10% for a period of time in a range of from about 2 hours to about 1 year the metal component comprising one or more metals chosen from nickel, chromium, vanadium, titanium, tantalum, zirconium, aluminum, molybdenum, organometallic complexes thereof, alloys thereof, or salts thereof, and
      the buffered aqueous solution has a pH in a range of from about 5 to about 9.

13. The method of claim 12, further comprising filtering the buffered aqueous solution.

14. The method of claim 12, wherein the acid or the base is added to the mixture in a drop-wise manner.

15. The method of claim 12, wherein the base NaOH.

16. The method of claim 12, wherein the acid is nitric acid.

17. The method of claim 12, wherein the buffered aqueous solution is in a container comprising at least one of a high density polyethylene and a low density polyethylene.

18. The method of claim 12, wherein the metal component that is added to the buffered aqueous solution and the water is a stock solution of one or more metals dissolved in acid.

19. The method of claim 12, wherein the metal component that is added to the buffered aqueous solution and the water is a powder.

20. A method of performing an assay, the method comprising:
   contacting a biological sample with a buffered aqueous solution, the buffered aqueous solution having a pH in a range of from about 5 to about 9 and comprising
      water; and
      a buffer comprising
         a citrate component having a concentration in the solution in a range of from about 5 mM to about 50 mM,
         a phosphate component having a concentration in the solution in a range of from about 2 mM to about 600 mM, and
         a metal component having a concentration in the solution in a range of from about 0.01 mM to about 100 mM wherein a total amount of the metal component in the solution does not increase or decrease more than 10% for a period of time in a range of from about 2 hours to about 1 year, the metal component comprising one or more metals chosen from nickel, chromium, vanadium, titanium, tantalum, zirconium, aluminum, molybdenum, organometallic complexes thereof, alloys thereof, or salts thereof
;and
receiving output data.

\* \* \* \* \*

UNITED STATES PATENT AND TRADEMARK OFFICE
CERTIFICATE OF CORRECTION

| | |
|---|---|
| PATENT NO. | : 11,119,094 B2 |
| APPLICATION NO. | : 16/139728 |
| DATED | : September 14, 2021 |
| INVENTOR(S) | : Miamidian et al. |

It is certified that error appears in the above-identified patent and that said Letters Patent is hereby corrected as shown below:

In the Claims

In Column 22, Line 33, in Claim 15, after "base", insert --is--

Signed and Sealed this
Fourth Day of January, 2022

Drew Hirshfeld
*Performing the Functions and Duties of the
Under Secretary of Commerce for Intellectual Property and
Director of the United States Patent and Trademark Office*